(12) United States Patent
Jean

(10) Patent No.: US 11,692,456 B2
(45) Date of Patent: *Jul. 4, 2023

(54) SYSTEM AND METHOD FOR DIAGNOSING A CONDITION OF AN ENGINE BASED ON VOLCANIC ASH

(71) Applicant: PRATT & WHITNEY CANADA CORP., Longueuil (CA)

(72) Inventor: Maurice Jean, Morin-Height (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/348,854

(22) Filed: Jun. 16, 2021

(65) Prior Publication Data

US 2022/0049620 A1 Feb. 17, 2022

Related U.S. Application Data

(63) Continuation of application No. 16/439,149, filed on Jun. 12, 2019, now Pat. No. 11,066,950.

(51) Int. Cl.
*G01M 15/14* (2006.01)
*F01D 21/00* (2006.01)
(Continued)

(52) U.S. Cl.
CPC .......... *F01D 21/003* (2013.01); *F01D 21/14* (2013.01); *G01M 15/14* (2013.01); *G01N 1/40* (2013.01);
(Continued)

(58) Field of Classification Search
CPC ..... G01M 15/14; G01N 1/40; G01N 15/0618; G01N 33/2888; G01N 2015/0053
See application file for complete search history.

(56) References Cited

U.S. PATENT DOCUMENTS 8,607,991 B2   12/2013   Lockledge et al.
8,666,570 B1    3/2014   Tillotson
(Continued)

FOREIGN PATENT DOCUMENTS

EP   3179392   6/2017
EP   2653677   2/2019

OTHER PUBLICATIONS

Thomas J. Grindle, "Engine Damage to a NASA DC-8-72 Airplane From a High-Altitude Encounter With a Diffuse Volcanic Ash Cloud", Technical Momerandum, Aug. 2003, US.
(Continued)

*Primary Examiner* — Eric S. McCall
(74) *Attorney, Agent, or Firm* — Norton Rose Fulbright Canada LLP

(57) ABSTRACT

A method and system for diagnosing a condition of an air-breathing aircraft engine are described. The method comprises obtaining a sample of lubricating fluid from the engine, filtering the sample to obtain a plurality of particles from the lubricating fluid, obtaining chemical composition data for the plurality of particles, determining a quantity of volcanic ash in the lubricating fluid by considering each one of the particles as composed partially of volcanic ash and partially of at least one other material and determining a first percentage of surface area of the particles covered by the volcanic ash and a second percentage of the surface area of the particles covered by the at least one other material, the volcanic ash having associated thereto a predetermined chemical composition, and diagnosing a condition of the engine based on the quantity of volcanic ash found in the lubricating fluid.

18 Claims, 5 Drawing Sheets

(51) Int. Cl.
*F01D 21/14* (2006.01)
*G01N 1/40* (2006.01)
*G01N 15/06* (2006.01)
*G01N 15/14* (2006.01)
*G01N 33/28* (2006.01)
*G01N 15/00* (2006.01)

(52) U.S. Cl.
CPC ......... *G01N 15/0618* (2013.01); *G01N 15/14* (2013.01); *G01N 33/2888* (2013.01); *G01N 2015/0053* (2013.01)

(56) References Cited

U.S. PATENT DOCUMENTS

| | | |
|---|---|---|
| 2013/0087708 A1 | 4/2013 | Tillotson |
| 2014/0053629 A1 | 2/2014 | Cahill |
| 2014/0121994 A1 | 5/2014 | Jean et al. |
| 2014/0157872 A1 | 6/2014 | Welland et al. |
| 2016/0370341 A1 | 12/2016 | Jean et al. |
| 2017/0159485 A1 | 6/2017 | Jean et al. |
| 2017/0307583 A1 | 10/2017 | Jean |
| 2019/0136767 A1 | 5/2019 | Farnum et al. |
| 2019/0234971 A1 | 8/2019 | Jean et al. |

OTHER PUBLICATIONS

Extended European Search Report dated Dec. 11, 2020 in counterpart EP application.

SYSTEM AND METHOD FOR DIAGNOSING A CONDITION OF AN ENGINE BASED ON VOLCANIC ASH

CROSS-REFERENCE TO RELATED APPLICATIONS

The present application is a continuation of U.S. patent application Ser. No. 16/439,149 filed on Jun. 12, 2019, the contents of which are hereby incorporated by reference.

TECHNICAL FIELD

The present disclosure relates generally to methods and systems for diagnosing a condition of an engine, for example based on a level of volcanic ash in a lubricating fluid.

BACKGROUND OF THE ART

Volcanic ash ejected into the atmosphere by explosive eruptions can have damaging effects on aircraft and their air-breathing engines. Ash particles can abrade forward-facing surfaces, including windscreens, fuselage surfaces, and compressor and fan blades. Ash contamination can also lead to failure of critical navigational and operational instruments. Moreover, the melting temperature of the glassy silicate material in an ash cloud is lower than combustion temperatures in modern aircraft engines. Consequently, ash particles sucked into an engine can melt quickly and accumulate as solidified deposits in cooler parts of the engine.

Therefore, improvements are needed.

SUMMARY

In accordance with a first broad aspect, there is provided a method for diagnosing a condition of an air-breathing aircraft engine. The method comprises obtaining a sample of lubricating fluid from the engine, filtering the sample to obtain a plurality of particles from the lubricating fluid, obtaining chemical composition data for the plurality of particles, determining a quantity of volcanic ash in the lubricating fluid by considering each one of the particles as composed partially of volcanic ash and partially of at least one other material and determining a first percentage of surface area of the particles covered by the volcanic ash and a second percentage of the surface area of the particles covered by the at least one other material, the volcanic ash having associated thereto a predetermined chemical composition, and diagnosing a condition of the engine based on the quantity of volcanic ash found in the lubricating fluid.

In accordance with another broad aspect, there is provided a system for diagnosing a condition of an air-breathing aircraft engine. The system comprises at least one processor and a memory having stored thereon program code executable by the at least one processor for obtaining chemical composition data for a plurality of particles filtered from a sample of lubricating fluid from the engine, determining a quantity of volcanic ash in the lubricating fluid by considering each one of the particles as composed partially of volcanic ash and partially of at least one other material and determining a first percentage of surface area of the particles covered by the volcanic ash and a second percentage of the surface area of the particles covered by the at least one other material, the volcanic ash having associated thereto a predetermined chemical composition, and diagnosing a condition of the engine based on the quantity of volcanic ash found in the lubricating fluid.

In accordance with yet another broad aspect, there is provided a non-transitory computer readable medium having stored thereon program code executable by a processor for carrying out the methods described herein.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Volcanic ash can reach high into the atmosphere and intersect airspace. Violent eruptions can reach the tropopause (at about 40,000 ft) and even penetrate into the stratosphere. Aircraft often fly just below the tropopause. Volcanic emissions remain in the atmosphere for different amounts of time, from hours to years, depending on the height they initially reach. It is estimated that 1 to 2% of all volcanic ashes will remain in suspension in the air, with the ashes having a diameter between 1-12 µm. Therefore, aircraft that fly over certain geographical regions which comprise or are adjacent to one or more volcanos are likely to take-in varying quantities of ash through the engine. The volcanic ash that enters through the engine of an aircraft may then make its way into the lubricating fluid of the engine.

There are described herein methods and systems for determining a quantity of volcanic ash in a lubricating fluid of an air-breathing aircraft engine. These methods and systems may be used for engine diagnostics, in particular for gas turbine engines. In some embodiments, the methods and systems described herein may be used for optimizing routes taken by aircraft in certain geographical regions, to reduce and/or minimize exposure of the aircraft to volcanic ash.

Figure 1:
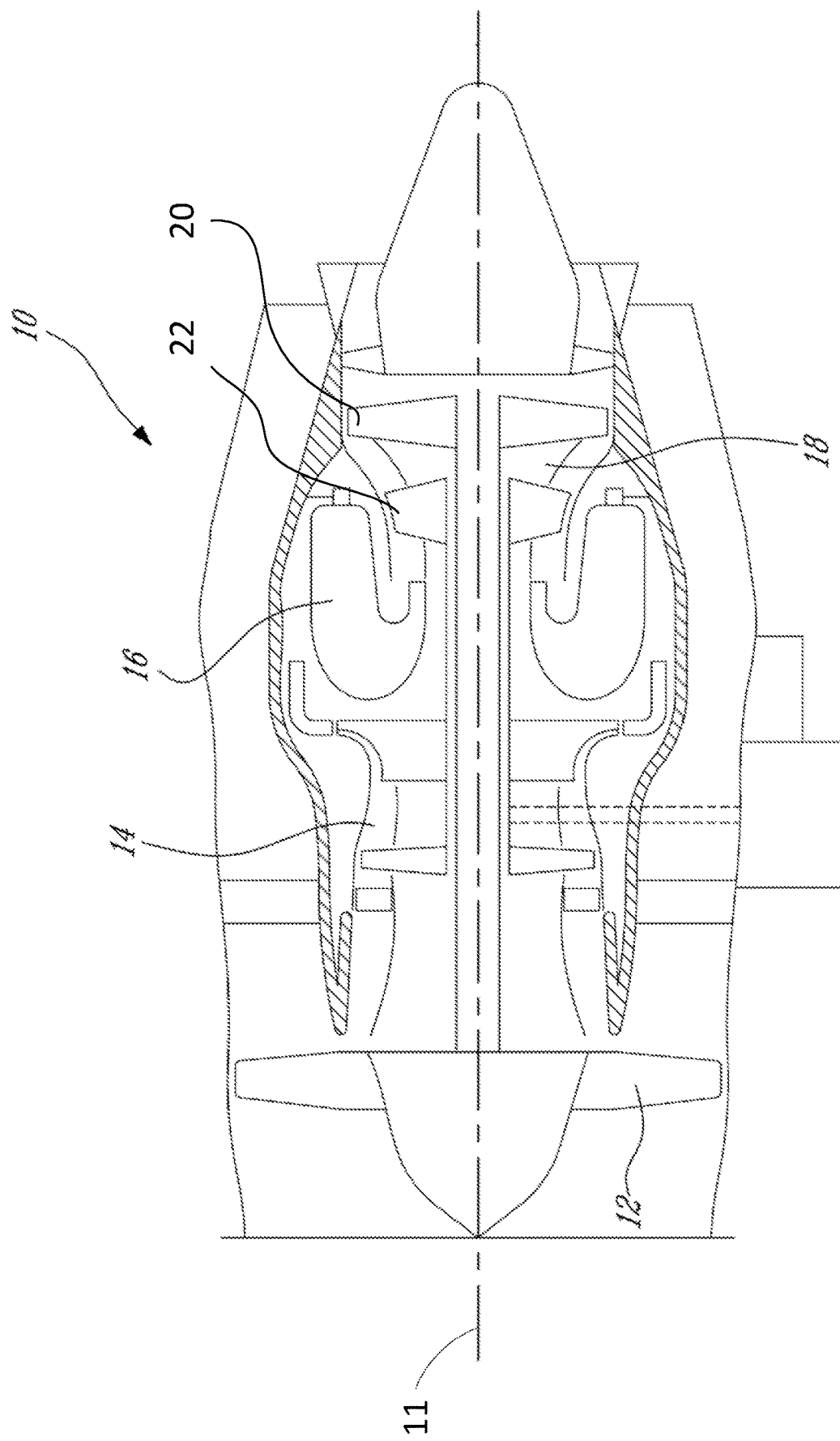
FIG. 1 illustrates an example of a gas turbine engine, in accordance with some embodiments.

FIG. 1 illustrates an example of a gas turbine engine 10 to which the methods and systems described herein may be applied. Note that while engine 10 is a turbofan engine, the methods and systems described herein may be applicable to turboprop, turboshaft, and other types of engines. Engine 10 generally comprises in serial flow communication: a fan 12 through which ambient air is propelled, a compressor section 14 for pressurizing the air, a combustor 16 in which the compressed air is mixed with fuel and ignited for generating an annular stream of hot combustion gases, and a turbine section 18 for extracting energy from the combustion gases. Axis 11 defines an axial direction of the engine 10. In some embodiments, a low pressure spool is composed of a low pressure shaft and a low pressure turbine 20. The low pressure shaft drives the fan 12. A high pressure spool is composed of a high pressure turbine 22 attached to a high pressure shaft, which is connected to the compressor section 14.

In some embodiments, the disclosed methods and systems may provide diagnostic and analytical tools based on analysis of particles in fluids, such as engine oil or other lubricants and may provide advance detection of premature wear on specific engine parts and/or detection of failure mechanisms. In some embodiments, the disclosed methods and systems may be suitable for failure prediction for gas turbine engines operating in the field. The disclosed methods and systems may be used for prediction of other wear events including prediction of events other than failure using analysis of any suitable lubricating fluid of the engine. The disclosed methods and systems may also be used to detect any abnormal behavior of an engine component in contact with a lubrication fluid system, for example.

Figure 2:
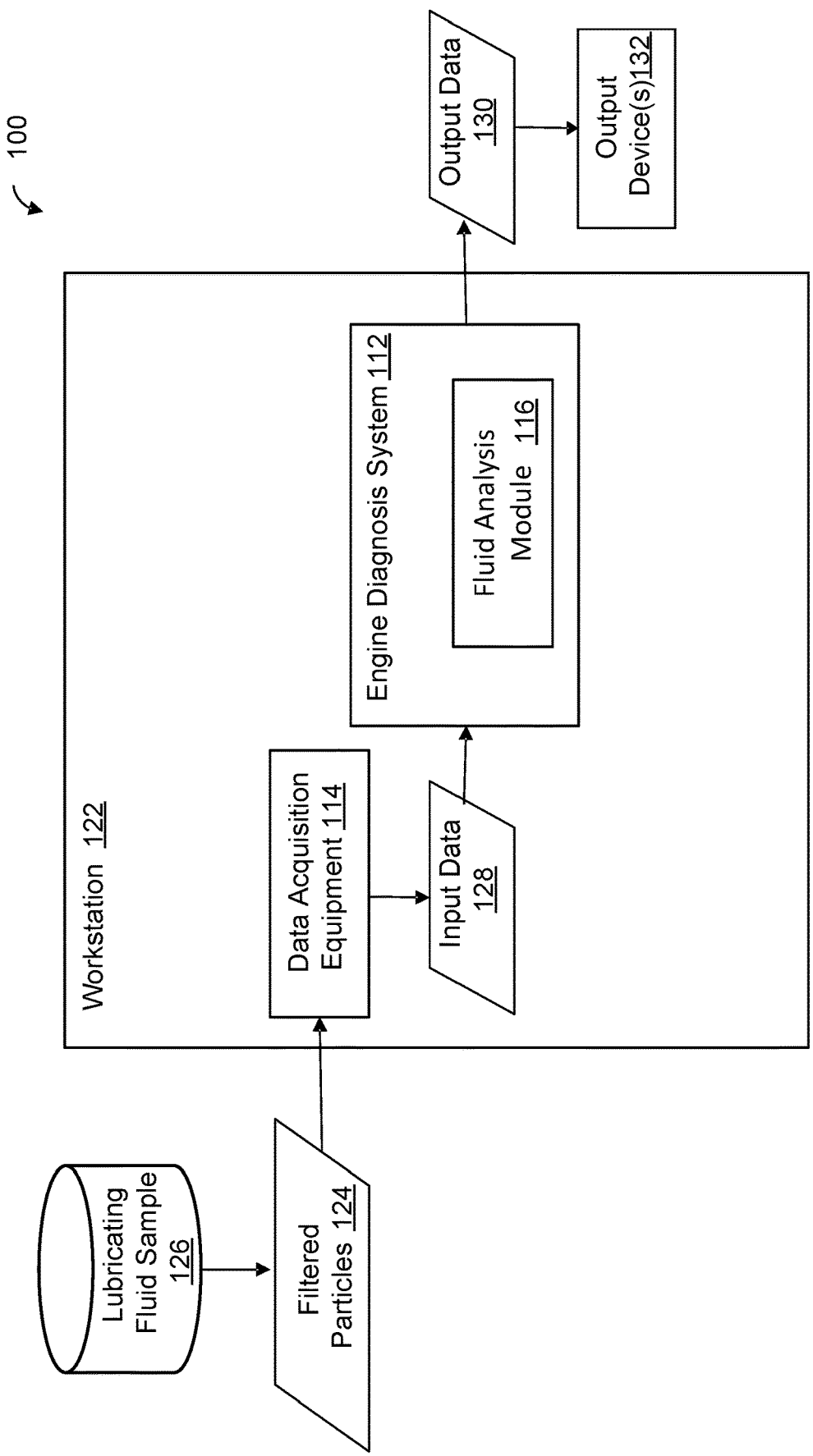
FIG. 2 is a block diagram of an example system for diagnosing a condition of an engine, in accordance with some embodiments.

FIG. 2 is a schematic diagram of an exemplary system 100 for diagnosing a condition of an engine such as the gas turbine engine 10 and which uses a fluid for lubricating some of its components, such as bearings. System 100 comprises an engine diagnostic system 112 and suitable data acquisition equipment 114 of known or other type. The engine diagnosis system 112 may comprise one or more fluid analysis modules 116, such as a fluid analysis module configured to determine a level of volcanic ash in a fluid sample. In some embodiments, a separate fluid analysis module 116 is provided to determine the level of each one of a plurality of components that may be found in a lubricating fluid.

The engine diagnosis system 112 and data acquisition equipment 114 may be considered part of a workstation 122, such as for a Scanning Electron Microscope (SEM). Accordingly, data acquisition equipment 114 may comprise an SEM and other related devices, although any other suitable devices/methods for extracting the relevant information from particles 124 filtered from lubricating fluid sample 126 may be used. In some embodiments, data acquisition equipment 114 may comprise an SEM and an X-Ray Fluorescence (XRF) detector for carrying out particle analysis. For example, data acquisition equipment 114 may comprise an automated SEM, such as that from Aspex Corporation. In some embodiments, the automated SEM may not require the presence of a human to select the particle(s) 124 that will be analyzed. In some embodiments, software and/or hardware included in workstation 122 may automatically recognize the presence of a particle 124 and may then automatically move a stage and/or an electron beam to the particle(s) 124 on which to perform the analysis.

System 100 may be used to conduct analysis of particles 124 filtered from lubricating fluid sample 126. Data acquisition equipment 114 may be used to analyze filtered particles 124 and generate input data 128. Input data 128 may be processed using engine diagnosis system 112 in order to generate output data 130. In some embodiments, output data 130 may be representative of a diagnosis of the condition of the engine and may be delivered to a user of system 100 or other authorized party via output device(s) 132 (e.g., one or more screens and/or printers) for displaying and/or otherwise providing a report of the result(s) of the diagnosis. System 100 may include one or more input devices (e.g., keyboard and mouse) for receiving user input, as well as one or more data ports and/or communication ports for receiving and/or transmitting data (e.g., wirelessly or through wired connections) from/to other processors, systems and/or devices. Processing of input data 128 by engine diagnosis system 112 may make use of reference data for comparison purpose. It is understood that processing of input data 128 may be performed using one or more processors external to workstation 122.

Figure 3:
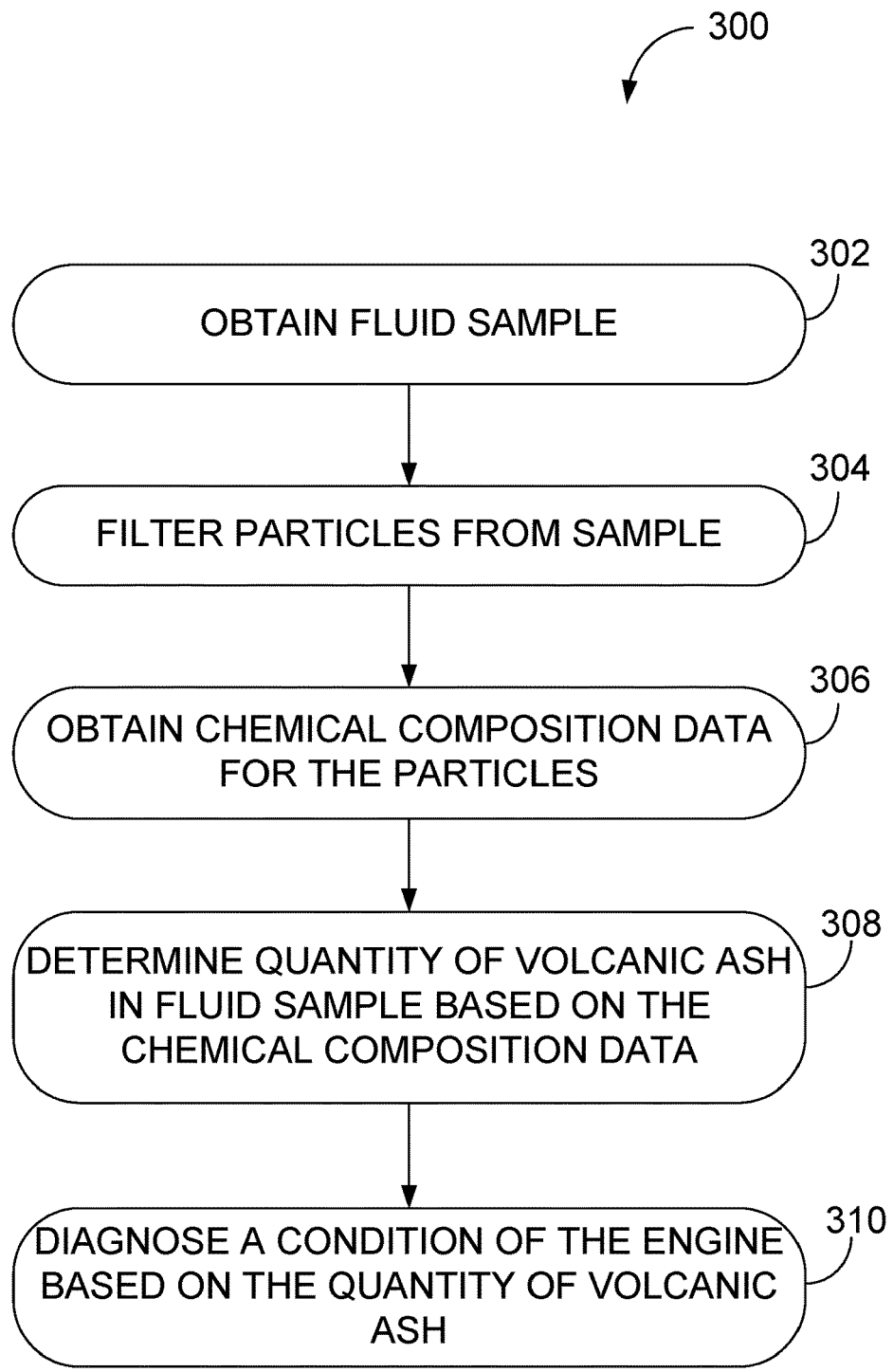
FIG. 3 is a flowchart of an example method for diagnosing a condition of an engine, in accordance with some embodiments.

Referring to FIG. 3, there is illustrated a flowchart of an example method 300 for diagnosing a condition of an engine, such as engine 10. At step 302, a sample fluid is obtained. For example, a sample of used lubricating fluid is obtained from the engine under diagnosis. In the case of a fluid sample from an aircraft engine, the fluid sample may be collected by an aircraft operator. More than one sample may be obtained. The amount of fluid sample obtained (e.g., 25 mL or less) may be selected in order to obtain a certain number of particles. For example, it may be known or expected that a given engine should have a certain density of particles in the fluid after a certain number of operating hours. The volume of fluid sample obtained may thus be determined in order to obtain an optimal quantity of particles. The frequency of sampling may be determined based on the operating hours per year, the maturity of the engine, the typical behavior of the engine type and/or the history of unscheduled engine removal for that engine type, for example. Any known or other engine fluid sampling method may be used, such as but not limited to pressurized line sampling, drop tube sampling, and drain port sampling.

At step 304, the sample of fluid is filtered to obtain a plurality of particles from the sample. Filtering may be performed using various techniques. For example, a collected fluid sample may be filtered using a very fine filter, such as a 0.22 μm filter, in order to filter out even very small particles (e.g., particles sized as small as 0.5 μm in diameter or smaller). Using such a filter, a sample of about 25 mL may produce a surface sample of about 16 mm in diameter. The particles obtained may range in size from about 0.5 μm to about 1600 μm, for example, although smaller or larger particles may also be obtained. The volume of fluid sample filtered and the size of the sample prepared may vary, such as according to the number of particles in the fluid. The volume of fluid sample that is filtered may be determined based on the type of engine and/or the expected normal levels of particles in the fluid. In some examples, the obtained density of particles may be 500 particles per $mm^2$. Other densities may also be used.

At step 306 chemical composition data is obtained for the particles. Each particle of the sample may be analyzed, for example, using an SEM equipped to perform x-ray spectroscopy, although any other suitable methods may also be used. A subset of the particles (e.g., 10% or less) may be analyzed while ensuring a good representation of the whole sample is captured. The analysis of the subset may be normalized to reflect the result for the full sample. For an average fluid sample, about 1500 to 2000 particles may be analyzed. Suitable image analyzer software, such as those conventionally used with SEM, may be used to collect data about particle composition. Analysis of each particle may produce a respective set of data for that particle, for example there may be up to 70 data points for each particle, the data describing various features of the particle (e.g., size, shape and composition, among others).

In some embodiments, obtaining the chemical composition data comprises receiving the chemical composition data from a data acquisition device, such as the SEM. In some embodiments, obtaining the chemical composition data comprises performing the acquisition of the data using a data acquisition device, such as the SEM.

At step 308, a quantity of volcanic ash in the fluid sample is determined based on the chemical composition data, the volcanic ash having associated thereto a predetermined chemical composition. Each particle is considered as composed partially of volcanic ash and partially of at least one other material, and the sample is analyzed to determine the level of volcanic ash therein.

In some embodiments, the volcanic ash is considered as a first alloy and the one or more other material making up the particle is considered as a second alloy.

In some embodiments, volcanic ash is categorized according to its silica content. Mafic ash (e.g. basalt) has a silica content between about 45% and about 52% and is rich in the minerals of feldspar, pyroxene, and olivine group. Felsic ash (e.g. rhyolite) has a silica content above about 69% and is rich in quartz and feldspar. Intermediate ash includes, for example, andesite (about 52% to about 63% silica) and dacite (about 63% to about 69% silica). In addition to silica, volcanic ashes may be composed of several oxides, such as ferrous, aluminum, magnesium, calcium, sodium, and several trace elements.

In some embodiments, volcanic ash is categorized according to its source. Studies have shown that the basic composition of the ash from Mount St Helens consists of approximately 65% $SiO_2$, 18% $Al_2O_3$, 5% $Fe_tO_3$, 2% MgO, 4% CaO, 4% $Na_2O$, and 0.1% S. This chemical composition is specific to the ash that comes from Mount St. Helens. The volcanic ash from another volcano, for example from Mount Stromboli in Italy, may therefore differ in chemical composition.

In order to determine a quantity of volcanic ash from a fluid sample, a specific volcanic ash composition of interest may be selected. In some embodiments, more than one volcanic ash composition is of interest. As such, the fluid sample may be analyzed in order to find any one of a plurality of volcanic ash compositions of interest. The various volcanic ash compositions may be predetermined and stored in one or more storage mediums, such as a memory, and accessed by the fluid analysis module 116.

Figure 4:
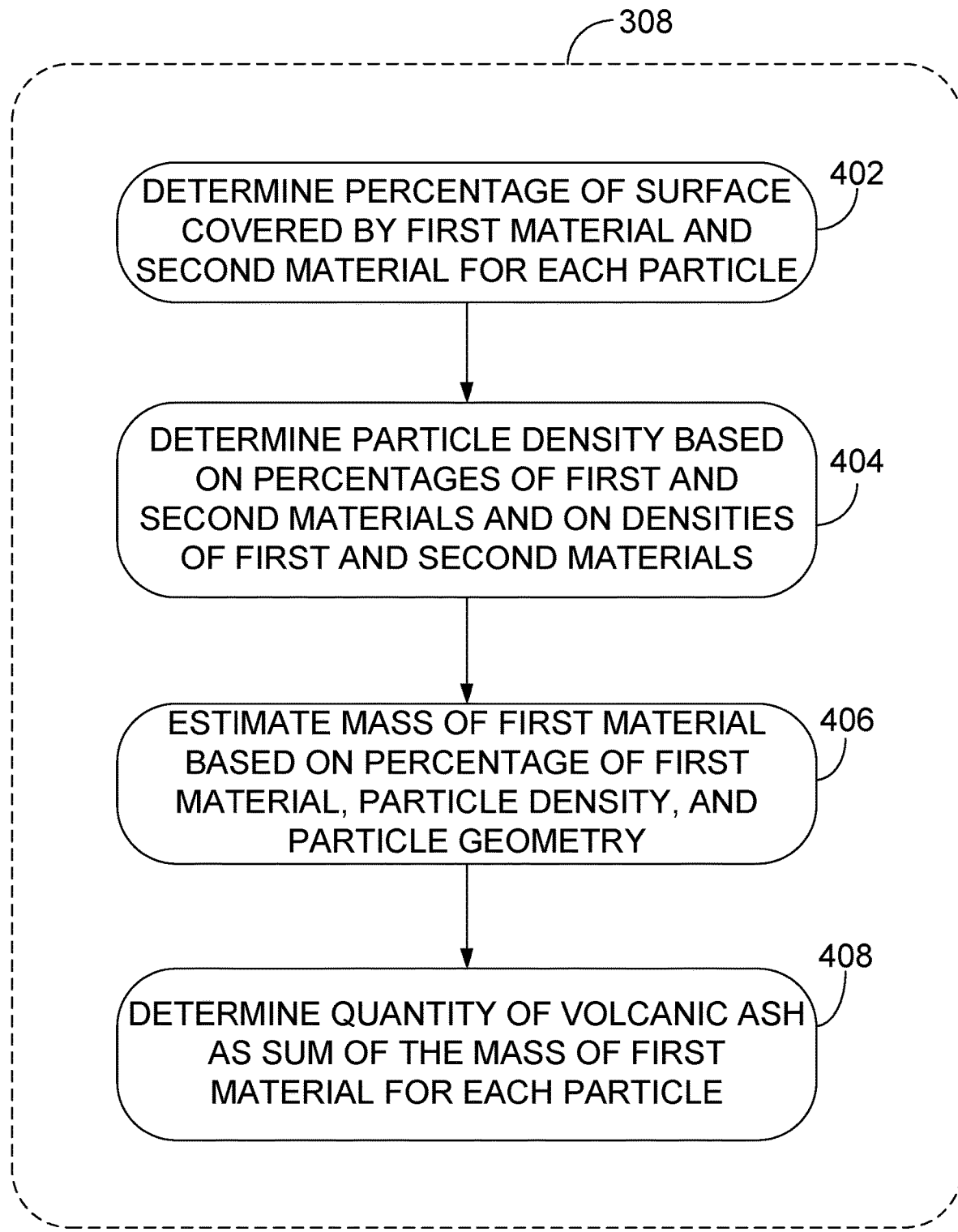
FIG. 4 is a flowchart of an example method for determining a quantity of volcanic ash in a fluid sample, in accordance with some embodiments.

In some embodiments, some of the particles in the fluid sample are composed in part of volcanic ash. The overall quantity of volcanic ash is thus determined by considering what percentage of surface area of the particles are covered by volcanic ash, and extrapolating from that percentage a mass of volcanic ash in the sample of fluid. An example embodiment is illustrated in FIG. 4.

At step 402, the percentage of surface area covered by a first material (the volcanic ash) and at least one other material (another alloy) are determined using:

$$100\% = S_1 + S_2 \quad (1)$$

$S_1$ is the percentage of volcanic ash and $S_2$ is the percentage of the other alloy making up the particle. For the purpose of the present example, it is assumed that the at least one other material corresponds to a second material. The values found for $S_1$ and $S_2$ may be measured using, for example, the data acquisition equipment 114 of the workstation 122. In some embodiments, the surface of the particle is covered by three or more alloys, including volcanic ash and two or more other materials. In such cases, equation (1) as well as equations (2) to (6) found below may be adapted accordingly.

At step 404, the particle density is determined based on the percentages of the first and second materials, and on the densities of the first and second materials:

$$D_p = \frac{s_1}{100} \times D_1 + \frac{s_2}{100} \times D_2 \quad (2)$$

$D_1$ and $D_2$ are the densities of the first and second materials, respectively, and $D_p$ is the density of the particle. The density $D_1$ is a known value associated with the specific chemical composition for volcanic ash. The density $D_2$ may be estimated based on the chemical composition of the second material, as measured.

At step 406, the mass of the volcanic ash (or first material) for the particle is determined based on the percentage of surface area of the particle it covers, the density of the particle, and the particle geometry. An estimated volume of the particle $V_p$ may be found using:

$$V_p = \frac{\text{Area} \times \text{smallest dimension} \times 3}{4} \quad (3)$$

The Area corresponds to the total surface area of a particle, such as 10 μm for a particle having dimensions of 2 μm×5 μm. The smallest dimension corresponds to the smallest of the two dimensions forming the Area, for example 2 μm in the example of a particle having dimensions of 2 μm×5 μm. With the volume ($V_p$) and the density ($D_p$) of the particle, the mass ($M_p$) may be found using:

$$M_p = V_p \times D_p \quad (4)$$

Using the mass of the particle, the mass of volcanic ash forming the particle ($M_1$) may be found using:

$$M_1 = \frac{\frac{s_1}{100} \times D_1}{D_p} \times M_p \quad (5)$$

At step 408, the quantity of volcanic ash in the sample is determined as the sum of the mass of volcanic ash for each particle:

$$\text{Volcanic ash}\left(\frac{mg}{L}\right) = \frac{\sum_{i=1}^{n} M_{1_i}}{V_s} \times 1000 \quad (6)$$

$V_s$ is the volume (in mL) of the fluid sample analyzed. Although provided in mg/L, the mass of volcanic ash may be obtained in other units, such as g/L or g/mL, as will be readily understood.

In some embodiments, only a subset of the particles from the sample will comprise volcanic ash. For the other particles, the value for $S_1$ will be set to zero and the result for $M_1$ will also be zero.

Referring back to FIG. 3, at step 310, once the quantity of volcanic ash in the fluid sample (or per given unit of fluid) is obtained, a condition of the engine may be diagnosed. The condition may comprise a number of remaining flight hours for the engine, an expected need for engine maintenance, a level of impact of the volcanic ash on the engine, a reduction in efficiency of the engine (i.e. 10%, 25%, 50%, etc), a reorganization of flight route, and the like.

Table 1 below is an example lookup table that may be used for engine diagnosis, for example by the engine diagnosis system 112.

TABLE 1

| Quantity of VA per unit of sample fluid | Remaining Flight Hours before next maintenance |
| --- | --- |
| 0-5 mg/L | >500 hrs |
| 6-10 mg/L | 250-500 hrs |
| 11-15 mg/L | <250 hrs |

Table 2 below is another example lookup table that may be used for engine diagnosis.

TABLE 2

| Quantity of VA per unit of sample fluid | Level of impact of VA on the engine |
| --- | --- |
| 0-5 mg/L | Low |
| 6-10 mg/L | Medium |
| 11-15 mg/L | High |

Reference data may be used to establish the impact of the volcanic ash on the engine. For example, reference engines from a common engine family having previously been exposed to a given level of volcanic ash may be analyzed to obtain the reference data. In some embodiments, the reference data is presented as one or more averages for all reference engines. The reference engines used for the reference data may form part of a common family with the engine under analysis. An engine family may be defined by any engine characteristic, such as type, model, operating principle, configuration, use, performance, thrust, torque, speed, power, etc. An engine family may also be defined by two or more engine features. For example, a family may correspond to turboprop engines, or turboprop engines in use in aircraft, or turboprop engines in use in aircraft and weighing between 150 and 450 kg. In another example, a family may correspond to a specific model or series, such as the PT-6 Series from Pratt & Whitney Canada. In some embodiments, a family may comprise sub-families, i.e. the family has at least one common engine characteristic and each sub-family has at least one additional common engine characteristic. Various combinations may be used.

In some embodiments, the reference data is presented as a percentage of selected engines matching one or more events. For example, out of 50 reference engines selected, i.e. comprising a similar level of volcanic ash per sample of lubricating fluid, the reference data may be presented as: 100% operated 200 hours without any problems, 91% operated 500 hours without any problems, 73% operated 600 hours without any problems, 10% operated 750 hours without any problems. Other events may also be used in this format.

In some embodiments, diagnosing a condition of the engine, as per step 310, comprises assigning a rating to the engine. Various types of engine rating systems may be used, and comprise any number of rating levels, such as two, three, four, and more. The ratings may be associated with an expected time until maintenance, or an expected time until breakdown. The rating may be determined using only the reference data of the reference engines, or a combination of reference data of the reference engines and historical/current data of the engine under analysis. For example, if the expected time until maintenance is 600 hours, the probability of achievement will be 73% based on the reference engines. Other rating systems may readily apply.

In some embodiments, the condition of the engine is used to determine whether an aircraft having a given engine should be deployed or not for a mission. In some embodiments, the condition of the engine is used to determine the route to use for a given mission. In some embodiments, the method 300 further comprises a step of taking a maintenance action based on the diagnosing, such as but not limited to issuing a report on the level of volcanic ash in the engine, setting a flag indicating a need for inspection, performing further inspection of the engine, and the like.

Figure 5:
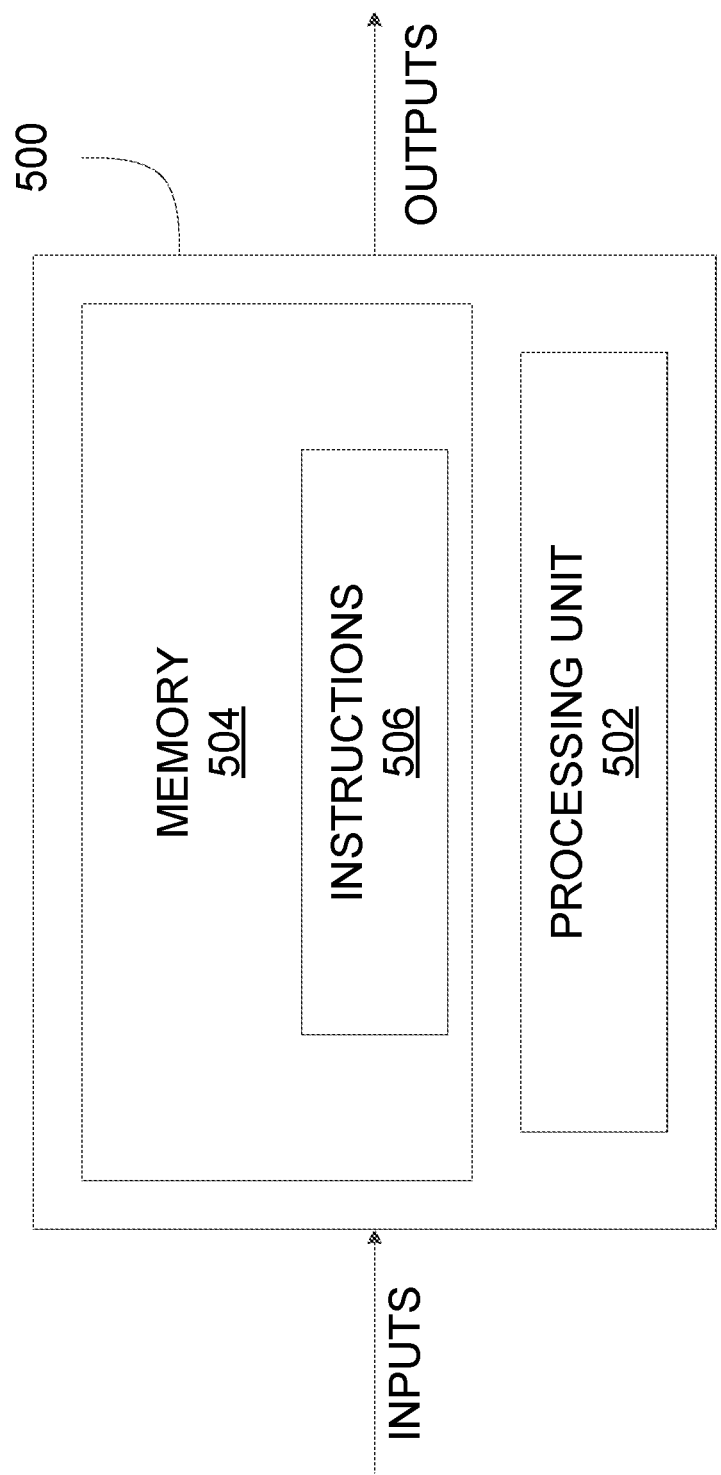
FIG. 5 is a block diagram of an example computing device for implementing a method for determining a level of volcanic ash in lubricating fluid, in accordance with some embodiments.

FIG. 5 is an example embodiment of a computing device 500 for implementing the engine diagnosis system 112 and/or the fluid analysis module 116 described above. The computing device 500 comprises a processing unit 502 and a memory 504 which has stored therein computer-executable instructions 506. The processing unit 502 may comprise any suitable devices configured to cause a series of steps to be performed such that instructions 506, when executed by the computing device 500 or other programmable apparatus, may cause the functions/acts/steps specified in the methods described herein to be executed. The processing unit 502 may comprise, for example, any type of general-purpose microprocessor or microcontroller, a digital signal processing (DSP) processor, a CPU, an integrated circuit, a field programmable gate array (FPGA), a reconfigurable processor, other suitably programmed or programmable logic circuits, or any combination thereof.

The memory 504 may comprise any suitable known or other machine-readable storage medium. The memory 504 may comprise non-transitory computer readable storage medium, for example, but not limited to, an electronic, magnetic, optical, electromagnetic, infrared, or semiconductor system, apparatus, or device, or any suitable combination of the foregoing. The memory 504 may include a suitable combination of any type of computer memory that is located either internally or externally to device, for example random-access memory (RAM), read-only memory (ROM), electro-optical memory, magneto-optical memory, erasable programmable read-only memory (EPROM), and electrically-erasable programmable read-only memory (EEPROM), Ferroelectric RAM (FRAM) or the like. Memory 504 may comprise any storage means (e.g., devices) suitable for retrievably storing machine-readable instructions 406 executable by processing unit 502. In some embodiments, the memory 504 stores one or more specific chemical composition for volcanic ash. In some embodiments, the memory 504 stores reference data from reference engines, and/or one or more lookup tables associating various levels of volcanic ash with corresponding engine conditions.

The methods and systems for diagnosing a condition of an engine and/or for determining a level of volcanic ash in a fluid sample as described herein may be implemented in a high level procedural or object oriented programming or scripting language, or a combination thereof, to communicate with or assist in the operation of a computer system, for example the computing device 500. Alternatively, the methods and systems for diagnosing a condition of an engine and/or for determining a level of volcanic ash in a fluid sample may be implemented in assembly or machine language. The language may be a compiled or interpreted language. Program code for implementing the methods and systems for diagnosing a condition of an engine and/or for determining a level of volcanic ash in a fluid sample may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems for diagnosing a condition of an engine and/or for determining a level of volcanic ash in a fluid sample may also be considered to be implemented by way of a non-transitory computer-readable storage medium having a computer program stored thereon. The computer program may comprise computer-readable instructions which cause a computer, or more specifically the processing unit 502 of the computing device 500, to operate in a specific and predefined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure.

Various aspects of the methods and systems for detecting a fault may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be obvious to those skilled in the art that changes and modifications may be made without departing from this invention in its broader aspects. The scope of the following claims should not be limited by the embodiments set forth in the examples, but should be given the broadest reasonable interpretation consistent with the description as a whole.

The invention claimed is:

1. A method for diagnosing a condition of an air-breathing aircraft engine, the method comprising:
   obtaining a sample of lubricating fluid from the engine;
   filtering the sample to obtain a plurality of particles from the lubricating fluid;
   obtaining chemical composition data for the plurality of particles;
   determining a quantity of volcanic ash in the lubricating fluid by considering each one of the particles as composed partially of volcanic ash and partially of at least one other material and determining a first percentage of surface area of the particles composed of the volcanic ash and a second percentage of the surface area of the particles composed of the at least one other material, the volcanic ash having associated thereto a predetermined chemical composition; and
   diagnosing a condition of the engine based on the quantity of volcanic ash found in the lubricating fluid.

2. The method of claim 1, wherein the at least one other material comprises one second material, and wherein the first percentage and the second percentage correspond to about 100% of the surface area.

3. The method of claim 1, wherein the predetermined chemical composition corresponds to a chemical composition for the volcanic ash associated with a geographical region.

4. The method of claim 1, further comprising determining a deployment of the aircraft engine based on the condition of the engine.

5. The method of claim 1, further comprising selecting a route for a mission for the aircraft engine based on the condition of the engine.

6. The method of claim 1, further comprising taking a maintenance action for the aircraft engine based on the condition of the engine.

7. The method of claim 1, wherein determining the quantity of volcanic ash in the lubricating fluid comprises determining particle density based on the first percentage and the second percentage and on a density of the volcanic ash and a density of the at least one other material.

8. The method of claim 7, wherein determining the quantity of volcanic ash in the lubricating fluid comprises estimating a mass of the volcanic ash per particle based on the first percentage and the second percentage, the particle density, and particle geometry.

9. The method of claim 8, wherein the geometry of the particle comprises a particle volume $V_p$ found using:

$$V_p = \frac{\text{Area} \times \text{smallest dimension} \times 3}{4};$$

where Area corresponds to a total surface area of a particle, and smallest dimension corresponds to a smallest of two dimensions forming the total surface area.

10. A system for diagnosing a condition of an air-breathing aircraft engine, the system comprising:
    at least one processor; and
    a memory having stored thereon program code executable by the at least one processor for:
      obtaining chemical composition data for a plurality of particles filtered from a sample of lubricating fluid from the engine;
      determining a quantity of volcanic ash in the lubricating fluid by considering each one of the particles as composed partially of volcanic ash and partially of at least one other material and determining a first percentage of surface area of the particles composed of the volcanic ash and a second percentage of the surface area of the particles composed of the at least one other material, the volcanic ash having associated thereto a predetermined chemical composition; and
      diagnosing a condition of the engine based on the quantity of volcanic ash found in the lubricating fluid.

11. The system of claim 10, wherein the at least one other material comprises one second material, and wherein the first percentage and the second percentage correspond to about 100% of the surface area.

12. The system of claim 10, wherein the predetermined chemical composition corresponds to a chemical composition for the volcanic ash associated with a geographical region.

13. The system of claim 10, wherein the program code is further executable for determining a deployment of the aircraft engine based on the condition of the engine.

14. The system of claim 10, wherein the program code is further executable for selecting a route for a mission for the aircraft engine based on the condition of the engine.

15. The system of claim 10, wherein the program code is further executable for taking a maintenance action for the aircraft engine based on the condition of the engine.

16. The system of claim 10, wherein determining the quantity of volcanic ash in the lubricating fluid comprises determining particle density based on the first percentage and the second percentage and on a density of the volcanic ash and a density of the at least one other material.

17. The system of claim 16, wherein determining the quantity of volcanic ash in the lubricating fluid comprises estimating a mass of the volcanic ash per particle based on the first percentage and the second percentage, the particle density, and particle geometry.

18. The system of claim 17, wherein the geometry of the particle comprises a particle volume $V_p$ found using:

$$V_p = \frac{\text{Area} \times \text{smallest dimension} \times 3}{4};$$

where Area corresponds to a total surface area of a particle, and smallest dimension corresponds to a smallest of two dimensions forming the total surface area.

\* \* \* \* \*